US012559720B2

(12) United States Patent

Veale et al.

(10) Patent No.: US 12,559,720 B2

(45) Date of Patent: Feb. 24, 2026

(54) MOBILIZATION AND COLLECTION OF PERIPHERAL BLOOD HEMATOPOIETIC STEM CELLS AND LYMPHOCYTES FROM DECEASED DONORS

(71) Applicants: The Regents of the University of California, Oakland, CA (US); ONELEGACY FOUNDATION, Los Angeles, CA (US)

(72) Inventors: Jeffrey L. Veale, Sherman Oaks, CA (US); Neil Kogut, Santa Monica, CA (US); Thomas David Mone, Los Angeles, CA (US)

(73) Assignees: The Regents of the University of California, Oakland, CA (US); ONELEGACY FOUNDATION, Los Angeles, CA (US)

( * ) Notice: Subject to any disclaimer, the term of this patent is extended or adjusted under 35 U.S.C. 154(b) by 728 days.

(21) Appl. No.: 17/269,369

(22) PCT Filed: Aug. 29, 2019

(86) PCT No.: PCT/US2019/048778

§ 371 (c)(1),
(2) Date: Feb. 18, 2021

(87) PCT Pub. No.: WO2020/047236

PCT Pub. Date: Mar. 5, 2020

(65) Prior Publication Data

US 2021/0189344 A1     Jun. 24, 2021

Related U.S. Application Data

(60) Provisional application No. 62/724,739, filed on Aug. 30, 2018.

(51) Int. Cl.
*C12N 5/0789*      (2010.01)
*A61K 35/17*      (2025.01)

(52) U.S. Cl.
CPC ............ *C12N 5/0647* (2013.01); *A61K 35/17* (2013.01)

(58) Field of Classification Search
None
See application file for complete search history.

(56) References Cited

U.S. PATENT DOCUMENTS

| | | | |
|---|---|---|---|
| 10,058,573 B1 * | 8/2018 | Morrow | A61K 31/4427 |
| 2002/0107469 A1 | 8/2002 | Bolan et al. | |
| 2015/0174195 A1 | 6/2015 | Shakhov et al. | |
| 2016/0120947 A1 | 5/2016 | Scadden et al. | |

FOREIGN PATENT DOCUMENTS

| | | | | |
|---|---|---|---|---|
| WO | WO-2014133729 A1 * | 9/2014 | ........... | A61K 31/365 |
| WO | WO-2016120310 A1 * | 8/2016 | ............. | A61K 31/40 |

OTHER PUBLICATIONS

Pantin J, Purev E, Tian X, Cook L, Donohue-Jerussi T, Cho E, Reger R, Hsieh M, Khuu H, Calandra G, Geller NL, Childs RW. Effect of high-dose plerixafor on CD34+ cell mobilization in healthy stem cell donors: results of a randomized crossover trial. Haematologica. Mar. 2017;102(3):600-609. (Year: 2017).*

Hopman RK, DiPersio JF. Advances in stem cell mobilization. Blood Rev. Jan. 2014;28(1):31-40. doi: 10.1016/j.blre.2014.01.001. Epub Jan. 14, 2014. PMID: 24476957; PMCID: PMC4068706. (Year: 2014).*

Hopman et al. ((Blood Rev. Vol 28. Issue 1. Jan. 2014. pp. 31-40) (Year: 2014).*

Haematologica. Mar. 2017; 102(3): 600-609. Prepublished online Oct. 19, 2016 (Year: 2016).*

Sosa et al., Transplantation. Feb. 1, 2023;107(2):504-510. doi: 10.1097/TP.0000000000004288. Epub Aug. 17, 2022 (Year: 2023)pp. 504-510.*

Hopman et al. (Blood Rev. Jan. 2014 ; 28(1): 31-40. doi:10.1016/j.blre.2014.01.001.) (Year: 2014).*

Pantin et al. (Haematologica. Oct. 19, 2016;102(3):600-609. doi: 10.3324/haematol.2016.147132) (Year: 2016).*

Machalinski et al., An Optimization of Isolation of Early Hematopoietic Cells From Heparinized Cadaveric Organ Donors. Transplantation Proceedings, 2003, vol. 35, No. 8, p. 3096-3100.

PCT International Search Report and Written Opinion dated Nov. 18, 2019 for PCT Application No. PCT/US19/48778.

Swearingen et al., AMD3100 (Plerixafor) as a Single-Dose Stem Cell Mobilizing Agent in Vascularized Composite Tissue Allograft Transplantation in a Canine Haploidentical Model. Journal of the American College of Surgeons, Oct. 2017, vol. 225, No. 4, Supplement 2, p. e143.

* cited by examiner

*Primary Examiner* — Fereydoun G Sajjadi
*Assistant Examiner* — Joel D Levin
(74) *Attorney, Agent, or Firm* — Gates & Cooper LLP

(57)          ABSTRACT

This invention describes new methods for the mobilization of human cells such as hematopoietic stem cells in bone marrow, and the subsequent collection of such cells from the peripheral blood of deceased donors. These methods produce quantities of hematopoietic stem cells that can be used in a multitude of possible applications without harming the deceased donor or the recovery of the deceased donor's organs for solid organ transplantation. The methods involve the administration of one or more mobilizing agents to mobilize bone marrow cells into the peripheral blood cells followed by the collection of cells via apheresis.

15 Claims, 2 Drawing Sheets

FIGURE 1A

| Enumeration Details | Chex Control 7/8/19 | BM | BM Negative Fraction | BM CD34s (5e5 cells) | Blood 7/4/19 9pm | Blood 7/5/19 1pm | Leukopak | Pre-Enrichment | Positive | Negative | Waste | Chamber | Chex Control 7/9/19 |
|---|---|---|---|---|---|---|---|---|---|---|---|---|---|
| Trucount (Trucount #events) | 4031 | 390 | | | 2276 | 608 | 74 | 111 | 8398 | 207 | 490 | 815 | 4252 |
| WBC | 60764 | 30885 | 94139 | 78181 | 136098 | 81936 | 51941 | 73453 | 57795 | 72052 | 35174 | 78480 | 62492 |
| Stem cells | 1051 | 89 | 430 | 54412 | 27 | 96 | 674 | 639 | 51342 | 89 | 387 | 836 | 1112 |
| Percent CD34+ of WBC (Stem Cells / Total WBC) | 1.73% | 0.29% | 0.46% | 69.60% | 0.02% | 0.12% | 1.30% | 0.87% | 88.83% | 0.12% | 1.10% | 1.07% | 1.78% |
| CD34/uL (Alive Stem cells x # beads per tube)/(Trucount x 100) | 128.80 | 112.73 | | | 5.86 | 78.00 | 4499.41 | 2843.84 | 3020.12 | 212.40 | 390.16 | 506.73 | 129.19 |
| Volume | | 130 | | | 1 | 1 | 447 | 150 | 100 | 250 | 2700 | 15 | |
| WBC/uL (WBC x # beads per tube)/(Trucount x 100) | 39121.00 | | | | | | 346741.27 | 326898.94 | 3399.71 | 171950.18 | 35461.13 | 47569.47 | |
| Total WBC | 5.09E+09 | | | | | | 1.55E+11 | 4.90E+10 | 3.40E+08 | 4.30E+10 | 9.57E+10 | 7.14E+08 | |
| Total CD34s | 1.47E+07 | | | | 5.86E+03 | 7.80E+04 | 2.01E+09 | 4.27E+08 | 3.02E+08 | 5.31E+07 | 1.05E+09 | 7.60E+06 | |

| | |
|---|---|
| #BEADS in Trucount tube | 49400 |
| | |
| From MANUAL count | |
| TNC in Positive Fraction | 2.85E+08 |
| CD34s in Positive Fraction | 2.53E+08 |
| TOTAL recovery | 13% |
| | |
| From TRUCOUNT count | |
| Total recovery | 15% |
| Recovery from Washes | 21% |
| Recovery from Enrichment Column | 71% |
| | |
| CD34 cells in the Waste and Chamber: | 1.06E+09 |

FIGURE 1B

MOBILIZATION AND COLLECTION OF PERIPHERAL BLOOD HEMATOPOIETIC STEM CELLS AND LYMPHOCYTES FROM DECEASED DONORS

CROSS REFERENCE TO RELATED APPLICATIONS

This application claims the benefit under 35 U.S.C. Section 119(e) of commonly-assigned U.S. Provisional Patent Application Ser. No. 62/724,739, filed on Aug. 30, 2018, and entitled "MOBILIZATION AND COLLECTION OF PERIPHERAL BLOOD HEMATOPOIETIC STEM CELLS FROM DECEASED DONORS" which application is incorporated by reference herein.

TECHNICAL FIELD

The present invention relates to methods for the mobilization and collection of cells from the peripheral blood of deceased donors.

BACKGROUND OF THE INVENTION

Hematopoietic stem cells (HSCs) in bone marrow can self-renew and differentiate into the myeloid, erythroid, megakaryocytic, and lymphoid cell lineages. HSCs can be mobilized from the bone marrow into circulating blood. Mobilized peripheral blood HSC's from living donors are widely used for autologous and allogeneic hematopoietic stem cell transplantation (HSCT) for a variety of malignant and non-malignant diseases.

There is increasing interest in combining HSCT and solid organ transplantation to achieve immune tolerance, defined as a state of immunological non-responsiveness to the grafted organ in the absence of immunosuppression. A number of published reports have demonstrated successful withdrawal of immunosuppression without rejection following combined kidney and HSC transplantation utilizing living donors. However, the majority of solid organ transplant (and vascularized composite allograft) recipients receive grafts from deceased donors. In order to extend the benefits of immune tolerance to this larger group, a reliable source of HSC's must be identified. Obtaining HSC's directly from the bone marrow of deceased donors is the focus of current investigation, but this approach presents a number of conceptual, technical, and logistical challenges.

There is a need in the art for additional methods of obtaining viable bone marrow derived hematopoietic stem and other cells that are useful in a variety of clinical applications including organ transplantation.

SUMMARY OF THE INVENTION

Bone marrow is the conventional source of HSC's from deceased donors. However, recovering HSC's from the bone marrow of deceased donors using conventional methods is a complex, multi-step process which involves resection of a large portion of the spine after organ recovery and transfer to a few highly specialized laboratories where the vertebrae are crushed and ground, and the cells are filtered, rinsed, and tumbled. Because of the removal of the spine, the bodies must often be reconstructed for viewing in the funeral home. Only a few highly specialized laboratories are capable of producing large numbers of HSC's from the bone marrow of deceased donors. Besides being disfiguring, this approach is laborious and unlikely to be widely adopted. In addition, there is frequent bacterial contamination of the cells due to exposure to the surgical field.

The present invention describes new approach to the recovery of cells from a donor, namely the mobilization of cells such as hematopoietic stem cells (HSCs) from the bone marrow of a deceased donor, and the subsequent collection of cells from the peripheral blood of the donor via apheresis. Embodiments of the invention have multiple applications beyond immune tolerance as there is a burgeoning demand for cells such as HSC's for a wide variety of research and therapeutic purposes.

The methods disclosed herein for the mobilization and collection of peripheral blood cells such as HSC's from deceased donors can produce quantities of viable HSC's useful in a multitude of applications without harming the ability to recover the donor's organs for transplantation. The invention provides a number of advantages over conventional methods for obtaining bone marrow from deceased donors including: less risk of contamination; reliance on routine clinical and laboratory techniques; does not require removal of a large portion of the axial skeleton and reconstruction of the body for viewing in a funeral home; and respects the dignity of the donor and the organ donation process and may be better accepted by the donor's family and loved ones. There are a number of other advantages of the invention, as well as clinical and research applications that are discussed below.

The invention disclosed herein has a number of embodiments. Embodiments of the invention include methods of administering to a deceased donor a mobilization agent such as plerixafor, followed by collecting cells from the peripheral blood of the donor via apheresis. Embodiments of the invention include the use of other mobilizing agents such as G-CSF (e.g. filgrastim or GRANIX) and GM-CSF (e.g. sargramostim) alone or in combination with plerixafor. In certain embodiments of the invention, the donor is administered only plerixafor as mobilization agent. In other embodiments of the invention, the deceased donor is administered one or more mobilization agents comprising not more than two doses of human granulocyte colony-stimulating factor (G-CSF). In these methods, cells collected from the peripheral blood can include, but are not limited to, $CD34^+$ stem/progenitor cells, mesenchymal stem cells, $CD133^+$ stem/progenitor cells, $CD3^+$ pan T cells, $CD4^+$ helper T cells, $CD8^+$ cytotoxic T cells, $CD14^+$ monocytes, $CD19^+$ B cells, $CD56^+$ NK cells, dendritic cells, macrophages, mononuclear cells, granulocytes, erythrocytes and platelets. In some embodiments of the invention, collecting mobilized peripheral blood hematopoietic stem cells and other cells from the donor via apheresis is performed less than 24 hours (e.g. 6-12 hours) following administration of a mobilization agent. In embodiments of the invention, apheresis can be performed on the donor for at least 2-12 hours; and/or so that at least 10, 15, 20, 24 or 30 liters of donor blood are processed via apheresis.

Embodiments of the invention can further comprise isolating one or more subsets of cell types from the apheresis product such as $CD34^+$ cells, T cells (e.g. $CD3^+$), dendritic cells, NK cells, and other immune cells. In certain embodiments of the invention, amounts of $CD34^+$ cells isolated from peripheral blood are sufficient to meet the threshold requirement for an allogenic stem cell transplant (e.g. $1.0 \times 10^6$ $CD34^+$ cells/kg recipient weight). Embodiments can also include the collection of HSC's from the donor's bone marrow after apheresis by aspirating bone marrow from a donor hip bone(s) and/or vertebrae into a syringe. Certain embodiments of the invention are combined with other medical procedures, for example removing an organ (e.g. a kidney, liver, heart, lung or vascularized composite allograft) from the donor for transplantation into a recipient patient.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIGS. 1A and 1B show data from a working embodiment of the invention in tabular form. FIG. 1A provides a first set of data from this working embodiment of the invention where CD34$^+$ cells were collected from peripheral blood and then isolated.

FIG. 1B provides a second set of data from this working embodiment of the invention, showing that $2.5 \times 10^8$ CD34$^+$ cells collected from peripheral blood were isolated in this embodiment of the invention.

DETAILED DESCRIPTION OF THE INVENTION

In the description of embodiments of the invention provided herein, it is to be understood that other embodiments may be utilized, and structural changes may be made without departing from the scope of the present invention. Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

In the methodologies disclosed herein, the "deceased donor" has experienced brain death. Brain death is defined as the death of the individual due to irreversible loss of function of the entire brain. It is the equivalent of circulatory death, which is due to irreversible loss of function of the circulatory system, which includes the heart. The brain death standards for adults and children that are widely accepted by the medical profession are the following guidelines: the American Academy of Neurology's 2010 Evidence-Based Guideline Update: Determining Brain Death in Adults; and the 2011 Guidelines for the Determination of Brain Death in Infants and Children, published by the Pediatric Section of the Society of Critical Care Medicine, the Sections of Neurology and Critical Care of the American Academy of Pediatrics and the Child Neurology Society. See also, U.S. Pat. No. 7,706,870, the contents of which are incorporated by reference.

Generally, the invention provides methods of mobilizing bone marrow cells in a deceased donor with an appropriate agent and then collecting cells from the peripheral blood of this donor. For example, embodiments of the invention include methods of administering plerixafor to the deceased donor, with or without G-CSF (e.g. filgrastim or GRANIX) or another mobilization agent, and then collecting mobilized cells from the peripheral blood of the deceased donor via apheresis. In one working embodiment of the invention, the deceased donor was administered a single dose of plerixafor, IUPAC name: 1-{[4-(1,4,8,11-tetrazacyclotetradec-1-ylmethyl)phenyl]methyl}-1,4,8,11 tetrazacyclotetradecane) as a mobilization agent. Plerixafor is well known in the art and disclosed in U.S. Patent Publication Nos. 20140219952, 20180207202 and 20140030308, the contents of which are incorporated by reference. In another working embodiment of the invention, the deceased donor was administered just two doses of human granulocyte colony-stimulating factor as a mobilization agent. G-CSF is well known in the art and disclosed in U.S. Patent Publication Nos. 20040028649, 20110135651, 20070036747, 20050186182 and 20140065706, the contents of which are incorporated by reference.

Embodiments of the invention include methods of collecting cells from a deceased donor, the methods comprising administering one or more mobilization agents to the deceased donor, wherein the one or more mobilization agents are administered to the deceased donor such that cells in bone marrow of the deceased donor are mobilized into the peripheral blood; and then collecting cells from peripheral blood of the deceased donor via apheresis. In typical embodiments of the invention, a mobilization agent comprises plerixafor; and/or a mobilization agent comprises G-CSF. Optionally in these methods, CD34$^+$ cells are collected; and at least about $1\text{-}2 \times 10^8$ viable CD34$^+$ cells are then isolated to at least 90-95% purity.

An illustrative embodiment of the invention is a method of collecting cells from a deceased donor, the method comprising administering one or more mobilization agents to the deceased donor, wherein the one or more mobilization agents comprise plerixafor, human granulocyte colony-stimulating factor (G-CSF), or a combination thereof. In such methods, the one or more mobilization agents are administered to the deceased donor such that cells in bone marrow of the deceased donor are mobilized into the peripheral blood; and the cells from peripheral blood (e.g. cells mobilized from the bone marrow) of the deceased donor are then collected via apheresis. In this context, a variety of apheresis methodologies are known in the art, for example those disclosed in U.S. Patent Publication Nos. 20160184361, 20180043082, 20170021083, 20060116271, 20050155932, 20050143684 and 20030195455, the contents of which are incorporated by reference.

In some embodiments of the invention, the deceased donor is administered a mobilization agent consisting essentially of plerixafor (e.g. a single dose of plerixafor). In other embodiments of the invention, the deceased donor is administered one or more mobilization agents comprising not more than two doses of human granulocyte colony-stimulating factor (G-CSF), either alone, or in combination with plerixafor. In some embodiments of the invention, the deceased donor is administered a first dose of a mobilization agent (e.g. plerixafor) followed by a first round of apheresis; and then a second dose of a mobilization agent followed by a second round of apheresis.

In some embodiments of the invention, collecting mobilized hematopoietic stem cells from the deceased donor via apheresis is performed less than 24 hours following administration of a mobilization agent (e.g. plerixafor). Embodiments of the invention include methods that further comprise collecting hematopoietic stem cells directly from deceased donor bone marrow following apheresis, wherein said collecting includes aspirating bone marrow from a deceased donor hip bone and/or vertebral bodies into a syringe.

In living donors, issues such as bone pain and the requirement to be relatively motionless for extended periods of time can hinder efforts to collect sufficient numbers of cells. In contrast, in deceased donors bone pain management strategies are not warranted and the donor is motionless. In view of this, in illustrative embodiments of the invention, the volume of blood processed from the deceased donor is greater than the volume of blood typically processed for living donors. Typically in the methods disclosed herein, at least 8, 10, 12, 16, 24 or 30 liters of deceased donor blood are processed via apheresis; and/or apheresis is performed on the deceased donor for at least 2-12 hours. In certain embodiments of the invention, cells collected via apheresis include at least one of; CD34$^+$ stem/progenitor cells, mesenchymal stem cells, CD133$^+$ stem/progenitor cells, CD3$^+$ pan T cells, CD4$^+$ helper T cells, CD8$^+$ cytotoxic T cells, CD14$^+$ monocytes, CD19$^+$ B cells, CD56$^+$ NK cells, dendritic cells, macrophages, mononuclear cells, granulocytes, erythrocytes and platelets. Optionally for example, the cells are CD34$^+$ cells; and amounts of CD34$^+$ cells isolated are sufficient to meet the threshold requirement for an allogeneic stem cell transplant (e.g. a target dose of 2×10$^6$ CD34$^+$ cells/kg recipient weight).

Embodiments of the invention include methods that further comprise removing tissue from the deceased donor for transplantation into a recipient patient. Typically in these methods, the tissue is a solid organ or a vascularized composite allograft. In some embodiments of the invention viable cells obtained from the deceased donor, and are further processed (e.g. isolated/purified) in a method selected to inhibit allograft rejection of the tissue (see, e.g. Chinen et al., J Allergy Clin Immunol. 2010 February; 125(2 Suppl 2): S324-S335).

In certain embodiments of the invention, cells collected from peripheral blood of the deceased donor are expanded to increase their numbers prior to being transplanted into a recipient patient. Embodiments of the invention can further comprise separating or isolating one or more subsets of cells collected from the peripheral blood via apheresis, for example CD34$^+$ cells. While typically compromising only 1.5% of bone marrow mononuclear cell population, CD34$^+$ cells are responsible for all lymphohematopoietic lineages and are now commonly used clinically as they have been shown to provide long term durable donor-derived host lymphohematopoietic reconstitution. In various embodiments, at least 1.0×10$^6$, 5×10$^6$, 1.0×10$^6$, 5×10$^7$, 1×10$^8$ or 2×10$^8$ CD34$^+$ cells are isolated to at least 90-95% purity. Crucially, the numbers of viable CD34$^+$ cells obtained in certain embodiments of the invention are sufficient to meet the threshold requirement for an allogenic stem cell transplant (e.g. a target dose of 2×10$^6$ CD34 cells/kg recipient weight).

Illustrative Working Embodiments of the Invention

In a first illustrative working embodiment of the invention, a 29 year old deceased donor was subcutaneously administered a single dose of a mobilization agent consisting essentially of plerixafor (0.24 kg/mg). Apheresis was started 8 hours following administration of the mobilization agent, with 24 liters of donor blood processed via apheresis over 8 hours. Albumin was given to support donor blood pressure which fell very briefly early in the procedure. Following administration of albumin, donor blood pressure rose and stabilized. The deceased donor tolerated the procedure well, exhibiting stable vital signs, oxygenation, urine output and the like. Whole body CT scans and routine hematology and serum chemistry panels performed before and after the procedure remained stable.

As shown by the data presented in Table 1 below, in this first working embodiment, CD34$^+$ cells were then isolated to about 90-95% purity, with more than 1.0×10$^8$ viable CD34$^+$ cells being isolated. As noted above, the numbers of CD34$^+$ cells obtained by this embodiment are sufficient to meet the threshold requirement for an allogenic stem cell transplant, for example a target dose of 2×10$^6$ CD34$^+$ cells/kg for a 50 kg recipient.

TABLE 1

RENAL LEUKOPAK RECOVERY

| | Vol-ume (mL) | TNC/mL | TNC | % via-bility | Total CD34+ % CD34+ | = % CD34+/ 100 x TNC *Total CD34+ |
|---|---|---|---|---|---|---|
| Leukopak Product | 460 | 3.23E+07 | 1.49E+10 | 99.5 | 0.87% | 1.29E+08 |
| Pre-Enrichment | 350 | 2.97E+07 | 1.04E+10 | 89 | 1.08% | 1.12E+08 |
| % Recovery from platelet wash and stain | | | | | | 87% |
| Positive (CD34) fraction | 47 | 2.60E+06 | 1.22E+08 | 95 | 95% | 1.16E+08 |
| Negative fraction | 250 | 4.03E+07 | 1.01E+10 | 96 | 0.03% | 3.02E+06 |
| Overall % CD34 recovery | | | | | | 90% |

In a second working embodiment, a 54 year old female registered organ donor was declared brain dead after suffering a cerebrovascular accident (CVA) with massive intracerebral hemorrhage. Initial complete blood count (CBC) and comprehensive metabolic panel tests were unremarkable. A computerized tomography (CT) scan showed hepatic lesions which on ultrasound were compatible with hemangiomas. The donor developed anuric renal failure. She was maintained on IV fluids and pressor agents.

This second donor received two doses of G-CSF (Granix) 10 ug/kg (780 ug) subcutaneously 7/3/19 at 1744 and 7/4/19 at 1700. She received plerixafor (Mozobil) 0.24 mg/kg (19 mg) subcutaneously 7/4/19 at 2310. CBC 7/5~6AM showed hemoglobin 11.4, WBC 46200 with 32% segs, 39% bands and platelets 97000. Apheresis was started at 7/5/19 0712 and was completed at 1644. Apheresis was well tolerated. A total volume of 447 ml was obtained. In addition, the donor underwent a bone marrow recovery and approximately 110 ml of bone marrow was obtained.

The apheresis unit and the bone marrow cells were then placed in a cooler at 4 degrees C. and transported by courier to a laboratory for further processing. The cells were kept at that temperature and were agitated over the next several days. On 7/8/19 the cells underwent CD34$^+$ selection on a Miltenyi Prodigy device.

The results of the cell processing in this second working embodiment of the invention are shown in the tables found in FIGS. 1A and 1B. FIGS. 1A and 1B show data from the second working embodiment of the invention in tabular form. FIG. 1A provides a first set of data from this working embodiment of the invention where CD34 cells were collected from peripheral blood and then isolated. FIG. 1B provides a second set of data from this working embodiment of the invention, showing that $2.5 \times 10^8$ CD34$^+$ cells collected from peripheral blood were isolated in this embodiment of the invention.

As shown in the tables found in FIGS. 1A and 1B, the yield of cells was from the second working embodiment was ~15× higher than the first working embodiment discussed above. In fact, there were so many cells that the capacity of the Prodigy apheresis device was exceeded. As a result, many cells were left behind in the machine so that the % recovery was low. Nevertheless, as shown in Table 1B, the final CD34$^+$ count was still high (~2.5× higher than that obtained in the first working embodiment) because the starting number was so high. Without being bound by a specific theory or mechanism of action, it is possible that the use of GCSF in addition to plerixafor resulted in mobilization of this higher number of peripheral blood CD 34$^+$ cells.

What is especially interesting is that in this second working embodiment, only two doses of GCSF plus a dose of plerixafor were given prior to apheresis. This is not a standard regimen for stem cell mobilization for autologous or allogeneic stem cell transplant (i.e. in living donors) where typically, 5 doses of GCSF are given prior to collection. This second working embodiment therefore also supports a novel method for mobilizing peripheral blood hematopoietic stem cells in living donors. The implications for a new dosing regimen here go beyond the collection of HSC's from deceased donors. In particular, this discovery represents an opportunity to improve upon the standard mobilization regimen for autologous and allogeneic hematopoietic stem cell transplantation. Such novel methods include, for example, a method of collecting cells from a living donor, the method comprising administering one or more mobilization agents comprising a dose of plerixafor and/or not more than two doses of human granulocyte colony-stimulating factor (G-CSF), such that cells from bone marrow in the living donor are mobilized into the peripheral blood; and then collecting cells from peripheral blood of the living donor via apheresis.

In the first and second working embodiments of the invention discussed above, the discovery that significant numbers of viable mobilized peripheral blood cells (e.g. at least $1.0 \times 10^8$ or $2.0 \times 10^8$ viable CD34$^+$ cells) can be obtained from deceased donors is surprising in view of what the art teaches in this field of technology. In particular, art in this field teaches that death events can damage tissues such as bone marrow. See, e.g. Bos et al., Kidney International (2007) 72, 797-805; doi:10.1038/sj.ki.5002400 which notes, for example that multiple immunomodulatory cytokines associated with physiologically abnormal state of brain death has a negative effect on transplant outcome. In this context it is known that hemodynamic changes can injure or damage bone marrow/hematopoietic stem cells (blood flow decrease). Moreover, brain death events such as the Cushing reflex, cytokine release and the catecholamine storm are known to disturb physiology including immune function. Similarly, pre-death events where a donor receives agents such as dopamine, epinephrine, nor-epinephrine and the like can lead to cellular necrosis. Also, before death, donors may receive numerous blood products (e.g. red blood cells and platelets) which can downregulate bone marrow cells. In addition, a single dose of single agent plerixafor and/or not more than two doses of human granulocyte colony-stimulating factor is generally not used and in conventional methods with living donors as these regimens are considered not adequate for mobilizing peripheral blood CD34$^+$ cells. Consequently, the discovery that significant numbers of viable mobilized peripheral blood cells can be obtained from deceased donors is unexpected in view of the conventional teachings in the art.

Embodiments of the invention include methods that collect bone marrow stem cells directly from donor bone marrow following apheresis, for example by aspirating bone marrow from a donor hip bone and/or vertebral bodies into a syringe. Certain embodiments of the invention include removing tissue from the donor for transplantation into a recipient patient, for example a solid organ or a vascularized composite allograft (e.g. kidneys, livers, hearts, lungs, limbs, faces, genitalia and the like). In some embodiments of the invention, viable CD34$^+$ cells and/or CD3$^+$ cells etc. are prepared for a procedure to induce immune tolerance after transplantation.

While only plerixafor is used in the first working embodiment of the invention disclosed herein, and G-CSF in combination with plerixafor is used in the second working embodiment of the invention disclosed herein, a number of other bone marrow cell mobilization agents and protocols that are well known in the art can be adapted for methods disclosed herein. Plerixafor, G-CSF and/or GM-CSF etc. may also be combined together and/or substituted with other mobilization agents known in the art (e.g. U.S. Pat. No. 5,925,568 discloses the use of MIPα for bone marrow cell mobilization and U.S. Pat. No. 5,843,438 discloses the use of anti-VLA-4 antibody and/or an anti-VCAM-1 for the purposes of HSC mobilization). Other mobilizing agents are described in Winker et al., Leukemia. 2012 July; 26(7): 1594-601. doi: 10.1038/leu.2012.17. Epub 2012; Hosoba et al., Blood 2014 123:310-311; and Cottler-Fox et al., Hematology 2003 2003:419-437; as well as U.S. Patent Publication Nos., 20020142462, 20050142103, 20110091928, 20160015786 and 20180355360, the contents of which are incorporated herein by reference.

Significance of and Unmet Need Addressed by Embodiments of the Invention

As discussed below, the disclosed invention is applicable in a variety of clinical applications including transplantation in patients who receive organs and tissues from deceased donors. The invention disclosed herein therefore addresses an unmet need in this field of technology, namely the need for methods and material that can decrease the risk of allograft failure and lifelong dependence on anti-rejection medications.

Solid organ transplantation (SOT) is often the only life-saving treatment option for patients with end stage organ disease. It has extended the lives and improved the quality of life of hundreds of thousands of patients with kidney, liver, heart, lung, and intestinal failure. In addition, the increasing use of vascularized composite allograft (VCA)—a relatively recent type of transplantation—is helping restore the functionality and quality of life of patients with severe trauma to the face, limbs, and genitalia (including many military veterans).

The major drawback of SOT and VCA is the need for lifelong immunosuppression. Potent immunosuppressive ("anti-rejection") drugs have a multitude of harmful side effects including infections, secondary malignancies, cardiovascular disease, diabetes, hypertension, hyperlipidemia, renal failure, hirsutism, etc. The need to adhere to a lifelong regimen of daily or twice daily medications and frequent laboratory monitoring impairs quality of life and often leads to non-compliance, especially in adolescents and young adults. Furthermore, these medications are expensive. Unfortunately, most allografts eventually fail, necessitating re-transplantation in many cases.

The "holy grail" of transplant researchers is the discovery of a reliable method(s) to induce a state of immune tolerance—that is, a state of immune unresponsiveness to the transplant graft in the absence of immunosuppression. The achievement of immune tolerance might make possible the goal of "one organ for life" and the elimination of immunosuppression and its attendant risks and expense. In addition, reduction or elimination of graft rejection can relieve demand for donor organs and increase organ availability. For instance, over 20% of the patients on the kidney transplant wait list have a failed allograft(s) and are awaiting re-transplantation. Reducing the need for a repeat transplant would free up organs for the many thousands of patients undergoing a first kidney transplant. Furthermore, successful immune tolerance protocols are likely to reduce the financial burden to the system by eliminating the costs associated with immunosuppressive medications, the complications of immunosuppression, and the management of graft rejection.

Considerable progress has been made towards fulfilling the promise of immune tolerance, especially following kidney transplantation. By combining kidney transplant with hematopoietic stem cell (HSC) transplant from the same living donor, researchers have reported that many patients can stop immunosuppression while maintaining excellent graft function and survival. In addition, studies suggest that quality of life is improved. Lastly, there is a preliminary signal of a cost savings. However, these trials have been open only to living donor transplant recipients. For the majority of transplant recipients who receive allografts from deceased donors, the potential benefits of immune tolerance approaches have been out of reach. A major impediment has been the lack of a widely available source of HSC's.

To address this impediment, artisans are investigating the use of HSC's obtained directly from the bone marrow of deceased donors (e.g. via collection of these cells from the spine). The conventional methods typically require the resection of a large portion of the spine followed by a long, complex, multi-step process to isolate the HSC's. Only a few highly specialized laboratories are capable of producing large numbers of HSC's from the bone marrow of deceased donors. Because of the removal of much of the spine, the bodies must often be reconstructed for viewing in the funeral home. Besides being disfiguring, this approach is laborious and unlikely to be widely adopted.

In order to overcome these problems, the invention disclosed herein provides novel methods to obtain HSC's from deceased donors—namely, the mobilization and collection of peripheral blood (PB) HSC's. The advantages of this procedure over conventional methods for obtaining bone marrow from deceased donors include less risk of contamination; the performance of only routine clinical and laboratory techniques; and eliminating the need to remove a large portion of the axial skeleton (which may be more acceptable to donor families). Establishing a reliable source of deceased donor HSC's has the potential to enable the two-thirds of transplant recipients who receive deceased donor allografts to enter clinical trials of immune tolerance. In addition, mobilized PB stem cells such as HSC's from deceased donors have applications in many other clinical and research settings where HSC's are needed.

In some embodiments of the invention, plerixafor can be used alone as a single agent for mobilization of PB HSC's in deceased donors. The advantage of plerixafor over GCSF—the standard drug for mobilizing HSC's—is its rapid onset of action. The peak onset of action is 6-10 hours after administration. In contrast, in living donors GCSF must be administered daily X 5 days before PB HSC collection. Plerixafor is FDA approved for use in conjunction with GCSF for patients with myeloma or non-Hodgkin lymphoma undergoing autologous stem cell transplant. There is relatively little experience with its use as a single agent and its effectiveness in this situation is not well-established. However, it appears to be effective when used as a single agent to mobilize PB HSC's from patients with sickle cell disease (not taking hydroxyurea) who are enrolled in gene therapy trials.

Mobilization and collection of PB HSC's from living donors has been done for decades and the process is well-described and validated. However, there are concerns as to the viability of these cells and such methods have never been attempted using deceased donors. Although large numbers of HSC's may be obtained from the bone marrow of deceased donors, the conventional approach requires resection of a large segment of the spine and a complex, highly specialized process to isolate the HSC's from the vertebrae. In this context, advantages of HSC's mobilized from deceased donor bone marrow include: methods where there is less risk of contamination; methods that employ standard clinical and laboratory procedures; methods that are not disfiguring, i.e. methods that may be more acceptable to donor families. Moreover, plerixafor is a rapidly acting mobilizing agent which is ideal for use in deceased donors. In this context, the successful collection of plerixafor mobilized PB HSC's from deceased donors will also extend the study of immune tolerance to the majority of transplant recipients. In addition, there are a number of other desirable clinical and research applications (e.g. inducible pluripotent stem cells, CRISPR gene edited HSC's, etc.)

Illustrating the significance of the invention disclosed herein, reports from artisans in this field of technology have demonstrated that the goal of immune tolerance is achievable. Namely, it is possible to withdraw immunosuppression and maintain graft function in a sizeable percentage of patients by combining kidney and HSC transplantation from the same living donor. The types of conditioning regimens, the risks, and the outcomes vary among the various trials at these centers. Nevertheless, the fundamental underlying feature of all the studies is the need for achievement of some level of chimerism—whether mixed or full, transient or durable. Chimerism gives rise to a change in the immunological milieu of the recipient such that alloreactive T cells undergo clonal deletion in the thymus and/or peripheral regulation or destruction.

Until now, only recipients of living donor kidney transplant have been considered for immune tolerance protocols. As a result, recipients of deceased donor organ transplants—the majority of transplant patients—have been excluded from pursuing this treatment approach. The major reason for this disparity has been the lack of a reliable, readily available source of HSC's from deceased donors.

As noted above, in order to overcome problems associated with limited sources of stem cells, there is increasing interest in using the bone marrow of deceased donors as the source of HSC's. The conventional technique for obtaining sufficient numbers of these cells for immune tolerance trials has been published. In brief, after recovery of donor organs, surgeons resect a large segment of the spine sometimes with the ilia. The specimens are sent to highly specialized laboratories where the vertebrae are crushed, filtered, rinsed and tumbled to obtain the HSC's. However, as noted earlier, this approach necessitates reconstruction of the spine for viewing of the body in funeral homes and highly specialized laboratory procedures available in only a few laboratories.

The conventional technique for mobilization and collection of PB HSC's from living donors has been in use for over 25 years. The standard approach is the administration of GCSF daily X 5 days followed by PB HSC collection via apheresis. However, a significant percentage of patients undergoing autologous stem cell collection fail to mobilize adequately with GCSF alone. Plerixafor is a short acting mobilizing agent which is FDA approved for use in conjunction with GCSF for mobilizing PB HSC's in patients undergoing autologous stem cell transplantation for multiple myeloma or non-Hodgkin lymphoma. In patients who fail to mobilize sufficient numbers of $CD34^+$ cells with GCSF alone (poor mobilizers), it has been found to be effective for increasing the yield of $CD34^+$ cells and reaching the target dose of $CD34^+$ cells used for transplantation into a recipient patient.

Prior to the enablement of the first working embodiment disclosed herein, one could not predict if the administration of a single agent, plerixafor, can function to mobilize PB HSC's from deceased donors. Prior to the enablement of the second working embodiment disclosed herein, one could not predict if the administration of not more than two doses of G-CSF can function to mobilize PB HSC's from deceased donors. Confirmation of the effectiveness of these mobilization strategies is a key discovery of this invention. In certain embodiments of the invention, Plerixafor has advantages over the use of G-CSF for mobilization and collection of HSC's from deceased donors. For example, plerixafor rapid onset of action (peak 6-10 hours) allows collection of HSC's within the window of the usual organ recovery process (60 hours average interval between identification of donor and organ recovery) and therefore additional time on life support is not necessary nor are there significant delays in organ recovery. This represents an advantage over the use of G-CSF as a mobilization agent which would require maintain the deceased donor on life support for a longer period of time. Moreover, plerixafor is easy to administer (a single subcutaneous dose) and is well tolerated with no major organ toxicity.

Past experience with the use of plerixafor as a single agent for mobilizing PB HSC's is limited and the results are mixed. Artisans have reported that ⅓ healthy donors fail to produce desired numbers of $CD34^+$ cells/kg following a standard dose of plerixafor (0.24 mg/kg) regardless whether given subcutaneously (approved route of administration) or intravenously. There may be greater efficacy with a higher dose of plerixafor and/or repeated doses. There have been several reports of successful mobilization of $CD34^+$ cells with single agent plerixafor in patients with sickle cell anemia entered into gene therapy trials. Interestingly, there have been some reports that single agent plerixafor mobilizes a unique graft from allogeneic donors containing increased numbers of plasmacytoid dendritic cells or NK cells, both of which may serve to decrease the risk of graft vs host disease in patients undergoing HSC transplant for hematological malignancies.

Embodiments of the invention can be adapted for use in transplantation procedures such as kidney transplants. The current standard of care for solid organ transplant and vascularized composite allografts is continuous immunosuppression for the life of the transplanted organ/tissue. How-ever, there are serious risks associated with the immunosuppressive drugs (infectious, secondary malignancies, metabolic, renal, cardiovascular, cosmetic, etc.) and increased burden to the patient due to the need to adhere to a complicated medical regimen and undergo frequent laboratory monitoring. The costs of the medications, the laboratory monitoring, and the treatment of side effects are high.

The goals of immune tolerance protocols are to eliminate the need for lifelong immunosuppression and the risk of graft rejection. There are indications from phase 2 trials that immune tolerance approaches combining kidney and HSC transplant from the same living donor may be preferable to standard of care in terms of graft survival, avoidance of side effects of immunosuppression, improved quality of life, and reduced cost.

Anticipated end users of this technology include transplant patients and transplant physicians and surgeons involved in the study of immune tolerance following solid organ or vascularized composite allograft transplantation. In addition to the uses in transplantation contexts discussed above, there are a number of alternative uses for bone marrow cells collected by the methods disclosed herein. For example, the invention provides a new source of HSC's and immune cells for applications including: biomedical research, inducible pluripotent stem cells, CRISPR gene edited stem cells. Moreover, these cells can be useful for HSC transplants in event of radiation disaster and a variety of malignant and non-malignant disorders. In addition, these cells can be useful as a source of CCR5 delta 32 mutated HSC's for HSC transplant for HIV, as well as for chimeric antigen receptor-T cells (e.g. in methods where chimeric antigen receptor T-cell therapy can have a synergistic role with hematopoietic stem cell transplantation).

PUBLICATIONS

All publications mentioned herein (e.g. U.S. Patent Publications 20050158858, 20090220453, 20110135651, 20120225028, 20130338183, 20150366914, 20160030478, 20170348375, 20170327573, and 20180185328), are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification. The following references include descriptions of methods and materials in this field of technology.

1. Strober S. Use of hematopoietic cell transplants to achieve tolerance in patients with solid organ transplants. Blood. 2016; 127(12):1539-43. PMCID: 4807420.
2. Kawai T, Leventhal J, Madsen J C, Strober S, Turka L A, Wood K J. Tolerance: one transplant for life. Transplantation. 2014; 98(2):117-21. PMCID: 4101034.
3. Montgomery R A. One kidney for life. American journal of transplantation: official journal of the American Society of Transplantation and the American Society of Transplant Surgeons. 2014; 14(7):1473-4.
4. Marcen R, Teruel J L. Patient outcomes after kidney allograft loss. Transplantation reviews. 2008; 22(1):62-72.
5. Kawai T, Sachs D H, Sprangers B, Spitzer T R, Saidman S L, Zorn E, Tolkoff-Rubin N, Preffer F, Crisalli K, Gao B, Wong W, Morris H, LoCascio S A, Sayre P, Shonts B, Williams W W, Jr., Smith R N, Colvin R B, Sykes M, Cosimi A B. Long-term results in recipients of combined HLA-mismatched kidney and bone marrow transplantation without maintenance immunosuppression. American journal of transplantation: official journal of the American Society of Transplantation and the American Society of Transplant Surgeons. 2014:14(7):1599-611. PMCID: 4228952.

6. Kawai T, Sachs D H, Sykes M, Cosimi A B, Immune Tolerance N. HLA-mismatched renal transplantation without maintenance immunosuppression. The New England journal of medicine. 2013; 368(19):1850-2. PMCID: 3760499.

7. Leventhal J, Abecassis M, Miller J, Gallon L, Tollerud D, Elliott M J, Bozulic L D, Houston C, Sustento-Reodica N, Ildstad S T. Tolerance induction in HLA disparate living donor kidney transplantation by donor stem cell infusion: durable chimerism predicts outcome. Transplantation. 2013:95(1):169-76. PMCID: 3531567.

8. Leventhal J R, Ildstad S T. Tolerance induction in HLA disparate living donor kidney transplantation by facilitating cell-enriched donor stem cell Infusion: The importance of durable chimerism. Human immunology. 2018; 79(5):272-6.

9. Scandling J D, Busque S, Dejbakhsh-Jones S, Benike C, Millan M T, Shizuru J A, Hoppe R T, Lowsky R, Engleman E G, Strober S. Tolerance and chimerism after renal and hematopoietic-cell transplantation. The New England journal of medicine. 2008; 358(4):362-8.

10. Scandling J D, Busque S, Lowsky R, Shizuru J, Shori A, Engleman E, Jensen K, Strober S. Macrochimerism and clinical transplant tolerance. Human immunology. 2018; 79(5):266-71. PMCID: 5924711.

11. Scandling J D, Busque S, Shizuru J A, Lowsky R, Hoppe R, Dejbakhsh-Jones S, Jensen K, Shori A, Strober J A, Lavori P, Turnbull B B, Engleman E G, Strober S. Chimerism, graft survival, and withdrawal of immunosuppressive drugs in HLA matched and mismatched patients after living donor kidney and hematopoietic cell transplantation. American journal of transplantation: official journal of the American Society of Transplantation and the American Society of Transplant Surgeons. 2015; 15(3):695-704.

12. Madariaga M L, Spencer P J, Shanmugarajah K, Crisalli K A, Chang D C, Markmann J F, Elias N, Cosimi A B, Sachs D H, Kawai T. Effect of tolerance versus chronic immunosuppression protocols on the quality of life of kidney transplant recipients. JCI insight. 2016; 1(8). PMCID: 4913782.

13. Erickson K F, Winkelmayer W C, Busque S, Lowsky R, Scandling J D, Strober S. A Cost Analysis of Tolerance Induction for Two-Haplotype Match Kidney Transplant Recipients. American journal of transplantation: official journal of the American Society of Transplantation and the American Society of Transplant Surgeons. 2016; 16(1):371-3.

14. Donnenberg A D, Gorantla V S, Schneeberger S, Moore L R, Brandacher G, Stanczak H M, Koch E K, Lee W A. Clinical implementation of a procedure to prepare bone marrow cells from cadaveric vertebral bodies. Regenerative medicine. 2011; 6(6):701-6. PMCID: 4159957.

15. Gorantla V S, Schneeberger S, Moore L R, Donnenberg V S, Zimmerlin L, Lee W P, Donnenberg A D. Development and validation of a procedure to isolate viable bone marrow cells from the vertebrae of cadaveric organ donors for composite organ grafting. Cytotherapy. 2012; 14(1):104-13. PMCID: 4162486.

16. Brave M, Farrell A, Ching Lin S, Ocheltree T, Pope Miksinski S, Lee S L, Saber H, Fourie J, Tornoe C, Booth B, Yuan W, He K, Justice R, Pazdur R. FDA review summary: Mozobil in combination with granulocyte colony-stimulating factor to mobilize hematopoietic stem cells to the peripheral blood for collection and subsequent autologous transplantation. Oncology. 2010; 78(3-4):282-8.

17. DiPersio J F, Stadtmauer E A, Nademanee A, Micallef I N, Stiff P J, Kaufman J L, Maziarz R T, Hosing C, Fruehauf S, Horwitz M, Cooper D, Bridger G, Calandra G, Investigators. Plerixafor and G-CSF versus placebo and G-CSF to mobilize hematopoietic stem cells for autologous stem cell transplantation in patients with multiple myeloma. Blood. 2009; 113(23):5720-6.

18. DiPersio J F, Micallef I N, Stiff P J, Bolwell B J, Maziarz R T, Jacobsen E, Nademanee A, McCarty J, Bridger G, Calandra G, Investigators. Phase II prospective randomized double-blind placebo-controlled trial of plerixafor plus granulocyte colony-stimulating factor compared with placebo plus granulocyte colony-stimulating factor for autologous stem-cell mobilization and transplantation for patients with non-Hodgkin's lymphoma. Journal of clinical oncology: official journal of the American Society of Clinical Oncology. 2009; 27(28):4767-73.

19. Devine S M, Vij R, Rettig M, Todt L, McGlauchlen K, Fisher N, Devine H, Link D C, Calandra G, Bridger G, Westervelt P, Dipersio J F. Rapid mobilization of functional donor hematopoietic cells without G-CSF using AMD3100, an antagonist of the CXCR4/SDF-1 interaction. Blood. 2008; 112(4):990-8.

20. Flomenberg N, Comenzo R L, Badel K, Calandra G. Plerixafor (Mozobil) alone to mobilize hematopoietic stem cells from multiple myeloma patients for autologous transplantation. Biology of blood and marrow transplantation: journal of the American Society for Blood and Marrow Transplantation. 2010; 16(5):695-700.

21. Boulad F, Shore T, van Besien K, Minniti C, Barbu-Stevanovic M, Fedus S W, Perna F, Greenberg J, Guarneri D, Nandi V, Mauguen A, Yazdanbakhsh K, Sadelain M, Shi P A. Safety and efficacy of plerixafor dose escalation for the mobilization of CD34(+) hematopoietic progenitor cells in patients with sickle cell disease: interim results. Haematologica. 2018; 103(5):770-7. PMCID: 5927989.

22. Hsieh M M, Tisdale J F. Hematopoietic stem cell mobilization with plerixafor in sickle cell disease. Haematologica. 2018; 103(5):749-50. PMCID: 5927977.

23. Lagresle-Peyrou C, Lefrere F, Magrin E, Ribeil J A, Romano O, Weber L, Magnani A, Sadek H, Plantier C, Gabrion A, Ternaux B, Felix T, Couzin C, Stanislas A, Treluyer J M, Lamhaut L, Joseph L, Delville M, Miccio A, Andre-Schmutz I, Cavazzana M. Plerixafor enables safe, rapid, efficient mobilization of hematopoietic stem cells in sickle cell disease patients after exchange transfusion. Haematologica. 2018; 103(5):778-86. PMCID: 5927997.

24. Tisdale J F, Pierciey F J, Kamble R, Kanter J, Krishnamurti L, Kwiatkowski J L, Thompson A A, Shestopalov I, Bonner M, Joseney-Antoine M, Asmal M, Walters M C. Successful Plerixafor-Mediated Mobilization, Apheresis, and Lentiviral Vector Transduction of Hematopoietic Stem Cells in Patients with Severe Sickle Cell Disease. Blood. 2017; 130(Suppl 1):990.

25. OPTN-HRSA. OPTN—U.S. Kidney Transplants Performed: Jan. 1, 1988-Apr. 30, 2018 [Report]: OPTN; 2018

[updated 2018; cited 2018 May 25, 2018]; Available from: https://optn.transplant.hrsa.gov/data/view-data-reports/build-advanced/.

26. Doyle M B, Vachharajani N, Wellen J R, Lowell J A, Shenoy S, Ridolfi G, Jendrisak M D, Coleman J, Maher M, Brockmeier D, Kappel D, Chapman W C. A novel organ donor facility: a decade of experience with liver donors. American journal of transplantation: official journal of the American Society of Transplantation and the American Society of Transplant Surgeons. 2014; 14(3): 615-20.

27. National Academies of Sciences E, and Medicine. Opportunities for Organ Donor Intervention Research: Saving Lives by Improving the Quality and Quantity of Organs for Transplantation. Washington, DC: The National Academies Press; 2017 Contract No.: Document Numberl.

28. Hongo D, Tang X, Baker J, Engleman E G, Strober S. Requirement for interactions of natural killer T cells and myeloid-derived suppressor cells for transplantation tolerance. American journal of transplantation: official journal of the American Society of Transplantation and the American Society of Transplant Surgeons. 2014; 14(11): 2467-77. PMCID: 4205183.

29. Hongo D, Tang X, Zhang X, Engleman E G, Strober S. Tolerogenic interactions between CD8(+) dendritic cells and NKT cells prevent rejection of bone marrow and organ grafts. Blood. 2017; 129(12):1718-28. PMCID: PMC5364338.

30. Hotta K, Aoyama A, Oura T, Yamada Y, Tonsho M, Huh K H, Kawai K, Schoenfeld D, Allan J S, Madsen J C, Benichou G, Smith R N, Colvin R B, Sachs D H, Cosimi A B, Kawai T. Induced regulatory T cells in allograft tolerance via transient mixed chimerism. JCI insight. 2016; 1(10). PMCID: 4951099.

31. Giralt S, Costa L, Schriber J, Dipersio J, Maziarz R, McCarty J, Shaughnessy P, Snyder E, Bensinger W, Copelan E, Hosing C, Negrin R, Petersen F B, Rondelli D, Soiffer R, Leather H, Pazzalia A, Devine S. Optimizing autologous stem cell mobilization strategies to improve patient outcomes: consensus guidelines and recommendations. Biology of blood and marrow transplantation: journal of the American Society for Blood and Marrow Transplantation. 2014; 20(3):295-308.

32. Pusic 1, Jiang S Y, Landua S, Uy G L, Rettig M P, Cashen A F, Westervelt P, Vij R, Abboud C N, Stockerl-Goldstein K E, Sempek D S, Smith A L, DiPersio J F. Impact of mobilization and remobilization strategies on achieving sufficient stem cell yields for autologous transplantation. Biology of blood and marrow transplantation: journal of the American Society for Blood and Marrow Transplantation. 2008; 14(9):1045-56.

33. Mone T D. Interval between identification of donor and organ recovery. In: Email Communication from TD Mone to N Kogut, May 30, 2018.

34. Schroeder M A, Rettig M P, Lopez S, Christ S, Fiala M, Eades W, Mir F A, Shao J, McFarland K, Trinkaus K, Shannon W, Deych E, Yu J, Vij R, Stockerl-Goldstein K, Cashen A F, Uy G L, Abboud C N, Westervelt P, DiPersio J F. Mobilization of allogeneic peripheral blood stem cell donors with intravenous plerixafor mobilizes a unique graft. Blood. 2017; 129(19):2680-92. PMCID: 5428459.

35. Lemery S J, Hsieh M M, Smith A, Rao S, Khuu H M, Theresa D, Viano J M, Cook L, Goodwin R, Boss C, Calandra G, Geller N, Tisdale J, Childs R. A pilot study evaluating the safety and CD34+ cell mobilizing activity of escalating doses of plerixafor in healthy volunteers. British journal of haematology. 2011:153(1):66-75. PMCID: 3879799.

36. Pantin J, Purev E, Tian X, Cook L, Donohue-Jerussi T, Cho E, Reger R, Hsieh M, Khuu H, Calandra G, Geller N L, Childs R W. Effect of high-dose plerixafor on CD34(+) cell mobilization in healthy stem cell donors: results of a randomized crossover trial. Haematologica. 2017; 102(3): 600-9. PMCID: 5394957.

37. Wong P P C, Kariminia A, Jones D, Eaves C J, Foley R, Ivison S, Couban S, Schultz K R Plerixafor effectively mobilizes CD56(bright) NK cells in blood providing an allograft predicted to protect against GvHD. Blood. 2018.

38. Karpova D, Brauninger S, Wiercinska E, Kramer A, Stock B, Graff J, Martin H, Wach A, Escot C, Douglas G, Romagnoli B, Chevalier E, Dembowski K, Hooftman L, Bonig H. Mobilization of hematopoietic stem cells with the novel CXCR4 antagonist POL6326 (balixafortide) in healthy volunteers-results of a dose escalation trial. Journal of translational medicine. 2017; 15(1):2. PMCID: 5209880.

CONCLUSION

This concludes the description of the illustrative embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A method of collecting cells from a deceased donor, the method comprising:

administering a mobilization agent to the deceased donor, wherein: the deceased donor is selected to have experienced brain death while maintaining cardiac and circulatory function, and the mobilization agent consists essentially of plerixafor; and the plerixafor is administered to the deceased donor such that CD34$^+$ cells in bone marrow of the deceased donor are mobilized into the peripheral blood; and collecting cells from peripheral blood of the deceased donor via apheresis, wherein:

collecting mobilized CD34$^+$ cells from the deceased donor via apheresis is performed less than 24 hours following administration of plerixafor; and at least $1.0 \times 10^8$ viable CD34$^+$ cells are collected from the deceased donor.

2. The method of claim 1, wherein the deceased donor is administered one or more mobilization agents comprising not more than two doses of human granulocyte colony-stimulating factor (G-CSF).

3. The method of claim 2, wherein the deceased donor is further administered plerixafor.

4. The method of claim 1, wherein the deceased donor is administered a single dose of plerixafor.

5. The method of claim 1, further comprising collecting CD34$^+$ cells directly from deceased donor bone marrow following apheresis, wherein said collecting includes aspirating bone marrow from a deceased donor hip bone and/or vertebral bodies into a syringe.

6. The method of claim 1, further comprising removing tissue from the deceased donor for transplantation into a recipient patient.

7. The method of claim 6, wherein the tissue is a solid organ or a vascularized composite allograft.

8. The method of claim 6, wherein viable CD34$^+$ and/or CD3$^+$ cells obtained from the deceased donor are further processed in a method to inhibit allograft rejection of the tissue.

9. The method of claim 1, wherein the deceased donor is administered a first dose of a mobilization agent consisting essentially of plerixafor followed by a first round of apheresis; and then a second dose of a mobilization agent consisting essentially of plerixafor followed by a second round of apheresis.

10. The method of claim 1, wherein cells collected from peripheral blood of the deceased donor are expanded to increase their numbers prior to being transplanted into a recipient patient.

11. A method of collecting cells from a deceased donor, the method comprising:

administering one or more mobilization agents to the deceased donor, wherein the deceased donor is selected to have experienced brain death while maintaining cardiac and circulatory function, and the one or more mobilization agents are administered to the deceased donor such that CD34$^+$ cells in bone marrow of the deceased donor are mobilized into the peripheral blood; and collecting cells from peripheral blood of the deceased donor via apheresis, wherein:

collecting mobilized CD34$^+$ cells from the deceased donor via apheresis is performed less than 24 hours following administration of plerixafor; and at least $1.0 \times 10^8$ viable CD34$^+$ cells are collected from the deceased donor.

12. The method of claim 11, wherein the method further comprises isolating the at least about $1.0 \times 10^8$ viable CD34$^+$ cells to at least 90-95% purity.

13. A method of mobilizing and collecting hematopoietic stem cells comprising:

administering to a deceased donor selected to have experienced brain death while maintaining cardiac and circulatory function, a mobilization regimen comprising a dose of plerixafor; and performing apheresis on the brain-dead donor to collect mobilized peripheral blood CD34+ hematopoietic stem cells, wherein:

the mobilization and the collection are completed less than 36 hours following the determination of brain death; and the collected hematopoietic stem cells are suitable for transplantation into a recipient receiving a solid organ from the deceased donor.

14. The method of claim 13, further comprising administering a dose of G-CSF.

15. The method of claim 13, wherein at least two doses of plerixafor are administered.

\* \* \* \* \*